United States Patent
Brandl et al.

(10) Patent No.: US 9,186,492 B2
(45) Date of Patent: Nov. 17, 2015

(54) MEDICAL APPARATUS WITH A SOCKET UNIT FOR THE CONNECTION OF A DEVICE FOR SUPPLYING MEDICAL FLUIDS

(71) Applicants: Matthias Brandl, Bad Koenigshofen (DE); Thomas Faulhaber, Bergrheinfeld (DE); Joern Hoermann, Heusweiler (DE); Franz Kugelmann, St. Wendel/Bliesen (DE); Goekhan Oerter, Weilmuenster (DE); Rafael Sterzer, Schweinfurt (DE)

(72) Inventors: Matthias Brandl, Bad Koenigshofen (DE); Thomas Faulhaber, Bergrheinfeld (DE); Joern Hoermann, Heusweiler (DE); Franz Kugelmann, St. Wendel/Bliesen (DE); Goekhan Oerter, Weilmuenster (DE); Rafael Sterzer, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 303 days.

(21) Appl. No.: 13/804,720

(22) Filed: Mar. 14, 2013

(65) Prior Publication Data

US 2013/0245531 A1    Sep. 19, 2013

Related U.S. Application Data

(60) Provisional application No. 61/611,637, filed on Mar. 16, 2012.

(30) Foreign Application Priority Data

Mar. 16, 2012   (DE) .......................... 10 2012 005 189

(51) Int. Cl.
*A61M 39/00*   (2006.01)
*A61M 39/10*   (2006.01)
*A61M 39/20*   (2006.01)
*A61M 1/16*   (2006.01)

(52) U.S. Cl.
CPC ............... *A61M 39/10* (2013.01); *A61M 1/168* (2013.01); *A61M 1/1656* (2013.01); *A61M 39/105* (2013.01); *A61M 39/20* (2013.01); *A61M 2039/1027* (2013.01); *A61M 2209/045* (2013.01)

(58) Field of Classification Search
CPC ... A61M 1/1656; A61M 1/168; A61M 39/10; A61M 39/105; A61M 39/1011; A61M 39/1055; A61M 39/14; A61M 39/16; A61M 39/165; A61M 39/20; A61M 2039/1027; A61M 2039/267; A61M 2209/045; F16K 11/02; F16K 11/072; F16K 11/078; F16K 11/085; F16K 11/0853
See application file for complete search history.

(56) References Cited

U.S. PATENT DOCUMENTS

| | | | |
|---|---|---|---|
| 2003/0168120 A1* | 9/2003 | Brehm et al. | 141/313 |
| 2010/0292673 A1* | 11/2010 | Korogi et al. | 604/533 |
| 2011/0196279 A1* | 8/2011 | Maierhofer et al. | 604/6.1 |
| 2013/0274702 A1* | 10/2013 | Miyasaka | 604/403 |

FOREIGN PATENT DOCUMENTS

| | | |
|---|---|---|
| EP | 0 575 970 A2 | 12/1993 |
| WO | 2009/074588 A1 | 6/2009 |
| WO | 2009/081196 A1 | 7/2009 |

OTHER PUBLICATIONS

International Preliminary Report on Patentability and Written Opinion in International Application No. PCT/EP2013/000774, dated Sep. 16, 2014.

* cited by examiner

*Primary Examiner* — Philip R Wiest
*Assistant Examiner* — Benjamin Klein
(74) *Attorney, Agent, or Firm* — Kenyon & Kenyon LLP

(57) ABSTRACT

A medical apparatus includes a socket unit for connecting a plug unit of a device for supplying medical fluids, in which the medical apparatus is in particular an extracorporeal blood treatment apparatus, for example an extracorporeal dialysis apparatus or an apparatus for peritoneal dialysis, or an apparatus for filling the device for supplying medical fluids. The socket unit comprises connection pieces for the connection of connectors of a plug unit, so that a flow connection can be produced for supplying or discharging a fluid. The connection pieces are surrounded by connection parts thereby forming rinsing chambers, in which the rinsing chambers are closed by closure pieces, said closure pieces being part of a closure body which is disposed rotatably on the socket unit.

15 Claims, 7 Drawing Sheets

MEDICAL APPARATUS WITH A SOCKET UNIT FOR THE CONNECTION OF A DEVICE FOR SUPPLYING MEDICAL FLUIDS

CROSS REFERENCE TO RELATED APPLICATIONS

The present application claims priority to U.S. Provisional Application Ser. No. 61/611,637, filed on Mar. 16, 2012, and Application No. DE 10 2012 005 189.1, filed in the Federal Republic of Germany on Mar. 16, 2012, each of which is expressly incorporated herein in its entirety by reference thereto.

FIELD OF INVENTION

The present invention relates to a medical apparatus with a socket unit for connecting a plug unit of a device for supplying medical fluids, wherein the medical apparatus is in particular an extracorporeal blood treatment apparatus, for example an extracorporeal dialysis apparatus or an apparatus for peritoneal dialysis, or an apparatus for filling or emptying the device for supplying medical fluids.

BACKGROUND INFORMATION

Various connectors are known for the connection of external components to medico-technical apparatuses. The access to the medico-technical apparatuses generally takes place by means of plugs, which are inserted into matching sockets of the medico-technical apparatuses. In this regard, the medico-technical apparatuses, which will be referred to generally below as medical apparatuses, comprise a corresponding socket unit, whilst the external components comprise a plug unit.

For the treatment of patients with kidney disease, use is made of blood treatment apparatuses, which include in particular the known extracorporeal dialysis apparatuses or apparatuses for peritoneal dialysis. The preparation of medical treatment fluids is required for cleaning the patient's blood. These include, for example, dialysing fluid or substitution fluid. In so-called automatic peritoneal dialysis (APD) or acute dialysis, the medical treatment fluids are automatically processed in the blood treatment apparatuses. The treatment fluids are prepared in fluid reservoirs, which are connected to the blood treatment apparatuses.

The fresh dialysing fluid is pumped from the fluid reservoir into the blood treatment apparatus. The fluid reservoir can already contain a concentrate which is diluted with water. In this case, the fluid reservoir only has to be filled with water. In this connection, therefore, water is understood to mean a medical fluid. It is also possible for a plurality of fluid reservoirs to be connected to a blood treatment apparatus, if a treatment fluid ready for use is produced in the treatment apparatus by mixing a plurality of fluids. The connection of the fluid reservoir to the blood treatment apparatuses again takes place with a plug unit, which is inserted into a socket unit of the blood treatment apparatus.

For the filling of devices for supplying dialysing fluid, apparatuses are known to which the devices for supplying dialysing fluid can be connected. The apparatuses for the filling therefore in turn comprise a socket unit which can be connected to the plug unit of the device for supplying dialysing fluid.

A device for supplying a treatment fluid is described for example in European Application No. EP 0 575 970 A2. The known device for supplying dialysing fluid comprises a bag for accommodating the fluid, to which a hose line is connected, which at its free end is connected to a plug. The dialysis apparatus comprises a socket into which the plug is inserted. Two flow connections can be produced with the plug and the socket, in order to convey fresh dialysing fluid from the bag into the dialysis apparatus and used dialysing fluid back into the bag. To secure the plug in the socket against slipping out, the plug comprises latching noses which engage in the recesses of the socket when the plug is fully inserted into the socket.

The connection of the device for supplying medical fluids to the blood treatment apparatus or an apparatus for the filling of the device for supplying medical fluids should be as straightforward and reliable as possible for the medical personnel. The socket unit should be able to be rinsed with a rinsing fluid for the purpose of disinfection.

A socket unit for a dialysis apparatus is described in International Patent Publication No. WO 2009/074588 A1, said socket unit being able to be rinsed with a rinsing fluid. The socket of the socket unit comprises a cylindrical housing body, in which a connection piece for a connector of a plug unit is disposed. For the purpose of rinsing, the housing body of the socket unit is closed by a closure piece, so that the cylindrical recess in the housing body forms a rinsing chamber through which the rinsing fluid flows. The closure piece is guided displaceably on the housing body of the socket unit between a first position in which the rinsing chamber is closed and a second position in which the rinsing chamber is open.

SUMMARY

A problem underlying the present invention is to simplify for the medical personnel the supplying of medical apparatuses, in particular blood treatment apparatuses, for example extracorporeal dialysis apparatuses or apparatuses for peritoneal dialysis, with medical fluids and to increase the reliability of the treatment.

The medical apparatus according to the present invention for the processing of medical fluids comprises a socket unit, whilst the device according to the present invention for supplying medical fluids comprises a plug unit.

The socket unit and the plug unit are characterised in that a flow connection between the medical apparatus on the one hand and the device for supplying medical fluids on the other hand can be produced in a straightforward and reliable manner with the two units.

In order to produce the flow connection, the socket unit comprises at least one connection piece, whilst the plug unit comprises at least one connector, so that a fluid-tight connection can be produced when the connection piece is connected to the connector. It is unimportant how the connection pieces and connectors are designed. The connection piece and the connector can for their part be plugs and sockets.

In order to supply, for example, fresh treatment fluid and to discharge, for example, used treatment fluid, a plurality of connection pieces and connectors can also be provided to produce a plurality of flow connections.

In the case of the socket unit according to the present invention, the at least one connection piece is surrounded concentrically by a connection part thereby forming a rinsing chamber, wherein the socket unit comprises a closure body with at least one closure piece for the closure of the at least one rinsing chamber.

The basic principle of the present invention lies in the fact that the closure body is mounted rotatably around a rotational axis, wherein the at least one closure piece on the closure body is disposed at a distance from the rotational axis. The closure body can be rotated between a first and a second rotational position.

In the first rotational position, the at least one closure piece and the at least one connection part lie on a common axis, so that a connection between the closure piece and the connection part can be produced for the closure of the rinsing chamber by a relative movement of the plug unit and the socket unit. In this connection, a relative movement of the closure piece and the connection part is understood to mean a movement of a displaceable closure piece onto a fixed connection part or a movement of a displaceable connection part onto a fixed closure piece. A reliable closure of the rinsing chamber can be achieved with the relative movement of the closure piece and the connection part, wherein the closure piece and the connection part can engage into one another.

In the second rotational position, the at least one closure piece and the at least one connection part or connection piece are disposed offset with respect to one another, so that a connection between the at least one connector of the plug unit and the at least one connection piece of the socket unit can be produced when the plug unit is inserted into the socket unit.

In a preferred exemplary embodiment, the socket unit comprises means for advancing the at least one connection part or connection piece out of the socket unit and for retracting the at least one connection part or connection piece into the socket unit. It is however also possible for the connection part to be fixed and the closure piece to be displaceable.

In a particularly preferred exemplary embodiment, the socket unit comprises a first connection piece for the connection of a first connector of the plug unit and a second connection piece for the connection of a second connector of the plug unit, so that a first flow connection for the supply of fluid and a second flow connection for the discharge of fluid can be produced, whilst the socket unit comprises a closure body with a first closure piece for the closure of the first rinsing chamber and a second closure piece for the closure of the second rinsing chamber of the socket unit, wherein the first and second closure piece are disposed on both sides of the rotational axis.

The closure body is preferably constituted such that the at least one rinsing chamber can be closed with the closure piece in the first rotational position and that the at least one connector of the plug unit can be connected to the at least one connection piece of the socket unit in the second rotational position. A further particularly preferred exemplary embodiment therefore provides for the formation of the closure body in such a way that the closure body comprises recesses disposed on both sides of the rotational axis in order to accommodate the connectors of the plug unit when the plug unit is inserted into the socket unit. The angle enclosed between the recesses and the connectors is preferably a right angle.

A further particularly preferred exemplary embodiment provides for an automatic connection of the connection piece and the connector. It is not therefore necessary to insert the plug unit fully into the socket unit. It is sufficient to insert the plug unit loosely into the socket unit. The fluid-tight connection of the connection piece and the connector then takes place automatically.

The socket unit preferably comprises means for the detachable connection of the plug unit to the socket unit, which are constituted such that the plug unit inserted initially only loosely into the socket unit is connected fixedly to the socket unit when the relative movement between the at least one connection piece of the socket unit and the at least one connector of the plug unit is performed.

The means for the detachable connection of the plug unit and the socket unit preferably comprise an accommodation piece, into which an extension piece of the plug unit can be inserted in a matching manner. The accommodation piece of the socket unit is preferably constituted as a tubular body into which the extension piece of the plug unit can be inserted.

The accommodation piece of the socket unit preferably comprises recesses to accommodate latching noses of the extension piece of the plug unit. A latch-type connection can thus be produced. The accommodation piece and the extension piece are however not yet thereby locked.

In order to lock the extension piece in the accommodation piece, the means for the detachable connection of the plug unit and the socket unit preferably comprises a pin-shaped body which can be introduced into the extension piece of the plug unit, so that the extension piece of the plug unit is splayed out in order to produce a fixed connection between plug unit and socket unit. The extension piece of the plug unit is thus secured against slipping out in the accommodation piece of the socket unit. In a particularly preferred exemplary embodiment, the locking of the extension piece and the accommodation piece takes place by the fact that the latching noses are secured in the recesses of the accommodation piece against slipping out by the splaying-out of the extension piece.

A further particularly preferred exemplary embodiment of the present invention provides for the automatic detection of the extension piece of the plug unit in the accommodation piece of the socket unit. The means for detecting the extension piece in the accommodation piece preferably comprise a spring-loaded sensing member, which is disposed in the socket unit in such a way that the sensing member is displaced against a spring tension when the extension piece of the plug unit is introduced into the accommodation piece of the socket unit. The displacement of the sensing member can be detected by known means. For example, electrical contacts which are closed or opened when the sensing member is displaced or a light barrier with which the position of the sensing member is detected can be provided for this purpose.

A particularly preferred exemplary embodiment makes provision such that the tubular accommodation piece is mounted rotatably on the socket unit, wherein the closure body is fixed to the accommodation piece of the socket unit. A unit with a particularly compact structure is thus created.

Exemplary embodiments of the present invention are explained below in greater detail with reference to the accompanying drawings.

DETAILED DESCRIPTION

Figure 1:
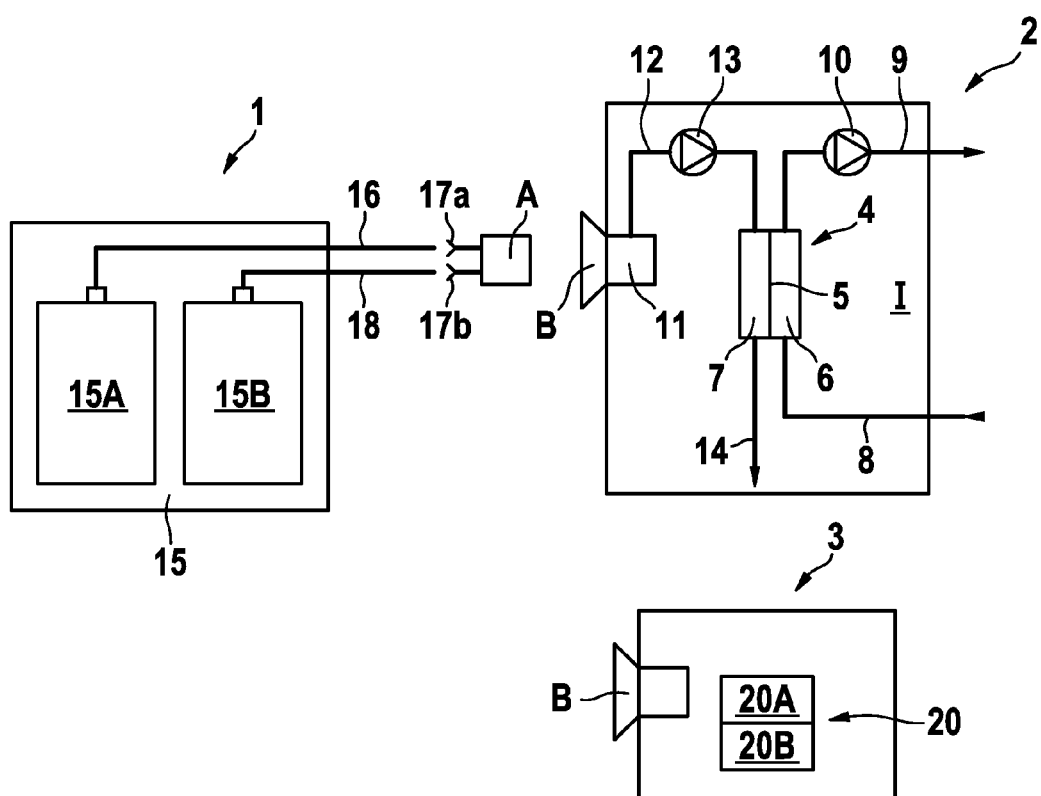
FIG. 1 shows a device for supplying a medical fluid, in particular dialysing fluid, together with the blood treatment apparatus and an apparatus for filling the device for supplying dialysing fluid, in a very simplified diagrammatic representation.

FIG. 1 shows, in a very simplified diagrammatic representation, a device 1 for supplying a medical fluid, in particular dialysing fluid, together with a blood treatment apparatus 2 and an apparatus 3 for filling the device for supplying dialysing fluid. Blood treatment apparatus 2 can be an extracorporeal dialysis apparatus or an apparatus for peritoneal dialysis. In the present exemplary embodiment, blood treatment apparatus 2 is a dialysis apparatus, which comprises a dialyser 4 which is divided by a semi-permeable membrane 5 into a blood chamber 6 and a dialysing fluid chamber 7. A blood supply line 8 leads from the patient to blood chamber 6 of dialyser 4, whilst a blood return line 9, into which a blood pump 10 is incorporated, leads from blood chamber 6 to the patient. Blood supply line and blood return line 8, 9 form together with blood chamber 6 extracorporeal blood circuit I of dialysis apparatus 2.

The fresh dialysing fluid is conveyed from a dialysing fluid reservoir 11 via a dialysing fluid supply line 12, into which a dialysing fluid pump 13 is incorporated, to dialysing fluid chamber 7 of dialyser 4, whilst used dialysing fluid flows away from the dialysing fluid chamber via a dialysing fluid discharge line 14.

Device 1, which in the present exemplary embodiment comprises two bags or canisters 15A and 15B, is used to supply fresh dialysing fluid. Both bags or canisters 15A, 15B form a unit 15, wherein bag 15A is filled with fresh dialysing fluid before the dialysis treatment and bag 15B is empty.

A supply line 16 leads from dialysing fluid bag 15A to the one connection 17a of a plug unit A, whilst a discharge line 18 leads from the other connection 17b of plug unit A to empty bag 15B.

For the preparation of dialysing fluid before the treatment, plug unit A is connected to a socket unit B which is provided on blood treatment apparatus 2, so that fresh dialysing fluid can be supplied via supply line 16 to dialysing fluid reservoir 11 and used dialysing fluid can be carried away via discharge line 18. The dialysing fluid can however also be supplied directly to dialysing fluid chamber 7 of the dialyser.

Device 1 for supplying dialysing fluid is filled at apparatus 3 with fresh dialysing fluid. Device 2 for supplying dialysing fluid can also be emptied with apparatus 3 for the filling. A tank 20A is used to accommodate fresh dialysing fluid and a tank 20B is used to accommodate used dialysing fluid. The required lines and pumps are not shown in the very diagrammatic representation.

Apparatus 3 for the filling and emptying of device 1 for supplying fresh and accommodating used dialysing fluid 1 comprises a socket unit B, to which plug unit A of device 1 for supplying dialysing fluid is connected. Socket unit B of blood treatment apparatus 2 and socket unit B of apparatus 3 for filling and emptying can be constituted identically or differently. In the present exemplary embodiment, socket units B are constituted identically. Both socket units B are constituted such that, by means of plug unit A of device 1 for supplying dialysing fluid, a fluid-tight flow connection can be produced with both apparatuses 2 and 3 in both directions for fresh and used dialysing fluid.

Plug unit A of device 1 for supplying dialysing fluid together with socket unit B is described in detail below by reference to FIGS. 2 to 7.

Figure 2:
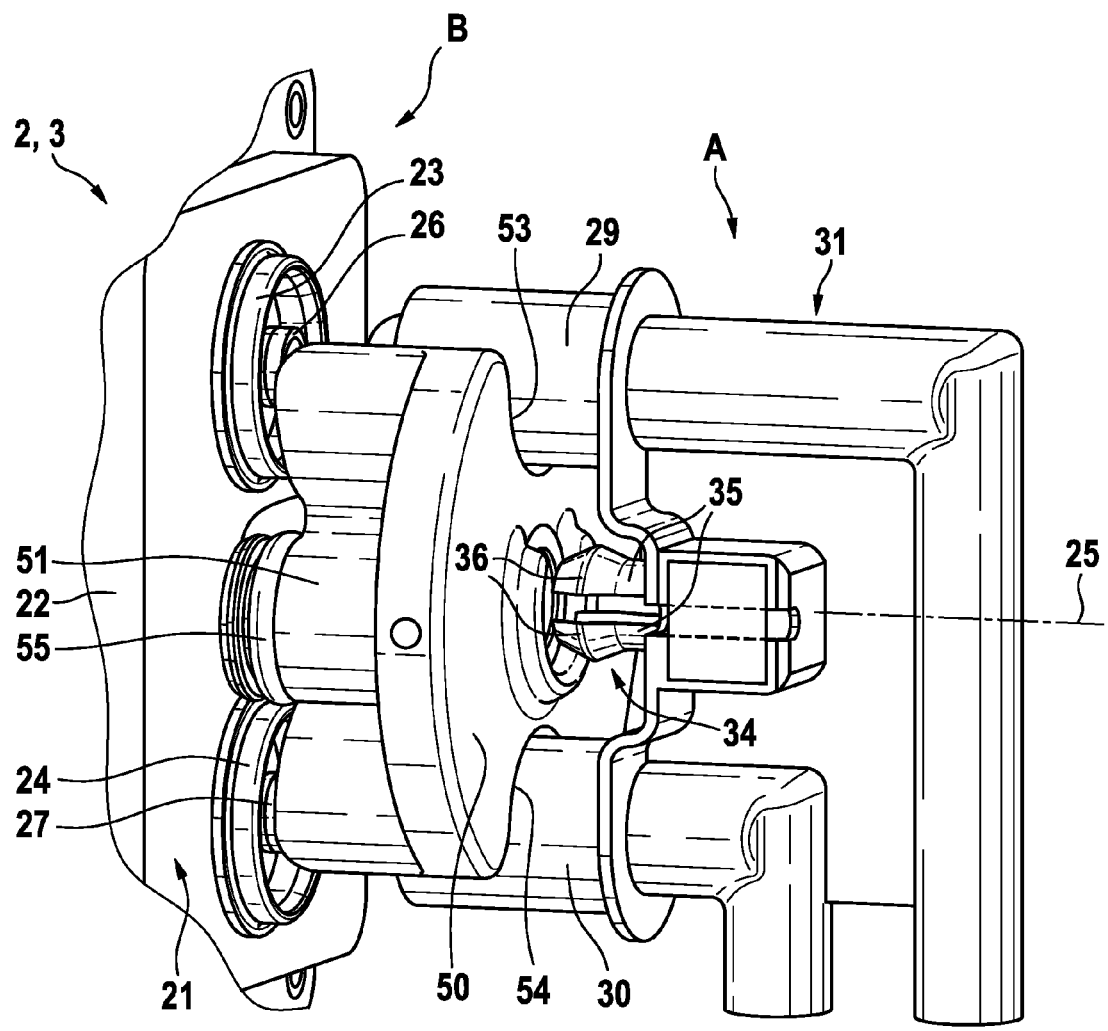
FIG. 2 shows the plug unit of the device for supplying dialysing fluid together with the socket unit of the blood treatment apparatus or the device for supplying dialysing fluid of FIG. 1 in a perspective representation.
Figure 3:
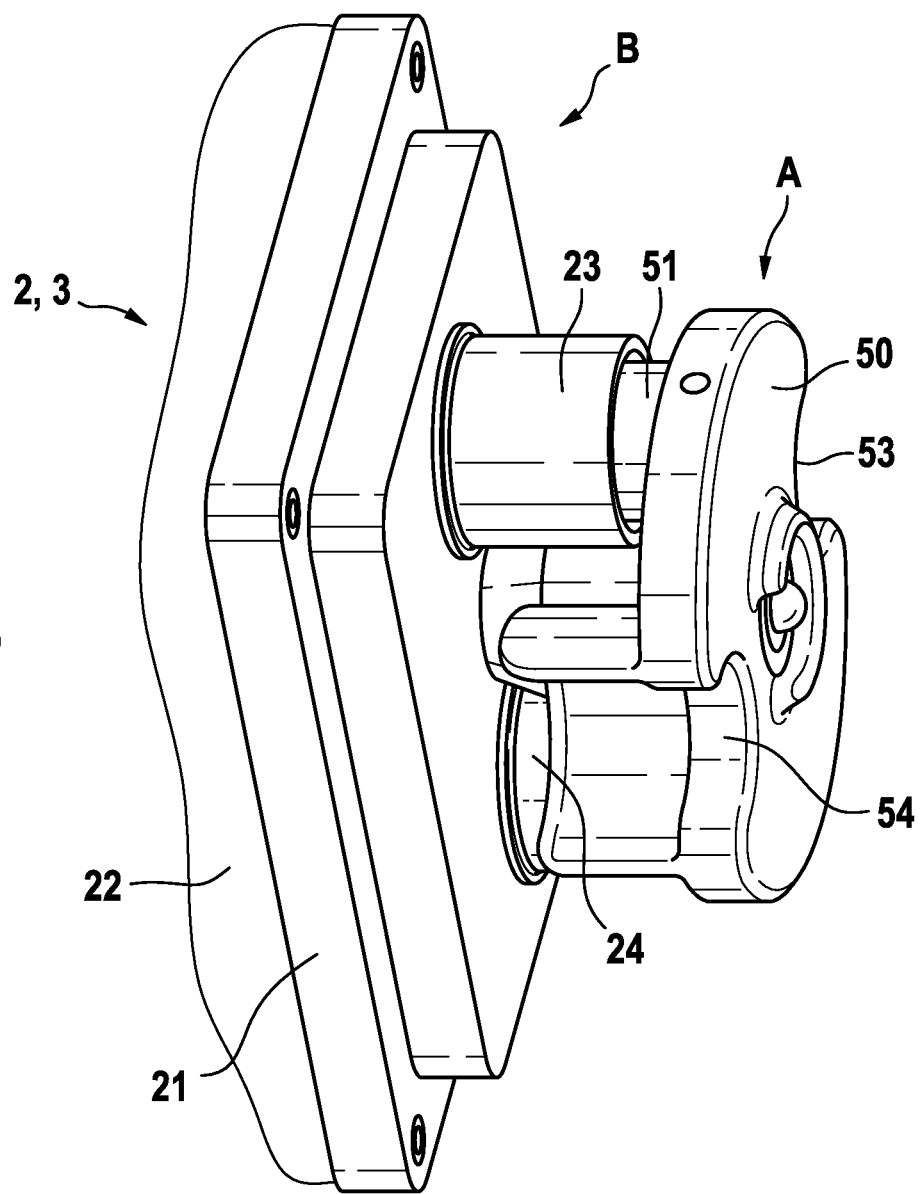
FIG. 3 shows the socket unit of FIG. 2 in a perspective representation, wherein the socket unit is prepared for a rinsing procedure.

FIGS. 2 and 3 show plug unit A and socket unit B in a perspective representation, whilst FIGS. 4 to 7 show plug unit A and socket unit B in a cross-sectional representation.

Socket unit B of blood treatment apparatus 2 can be part of a replaceable treatment cassette (not represented). Socket unit B can however also be part of a non-replaceable unit.

FIG. 2 shows socket unit B together with plug unit A in a perspective representation. By means of plug unit A, device 1 for supplying dialysing fluid can be connected on the one hand to apparatus 3 for the filling and emptying and on the other hand to blood treatment apparatus 2.

Socket unit B comprises a housing body 21, which is inserted in a housing wall 22 of blood treatment apparatus 2 or apparatus 3 for the filling. Provided in housing body 21 of socket unit B are two cylinder connection parts 23, 24, which are disposed in a common plane on both sides of central axis 25 of the socket unit. Cylindrical connection parts 23, 24 each surround concentrically a connection piece 26 and 27 respectively, wherein connection piece 26 is used for supplying fresh dialysing fluid and connection piece 27 is used for carrying away used dialysing fluid (FIGS. 4 to 7).

Figure 7:
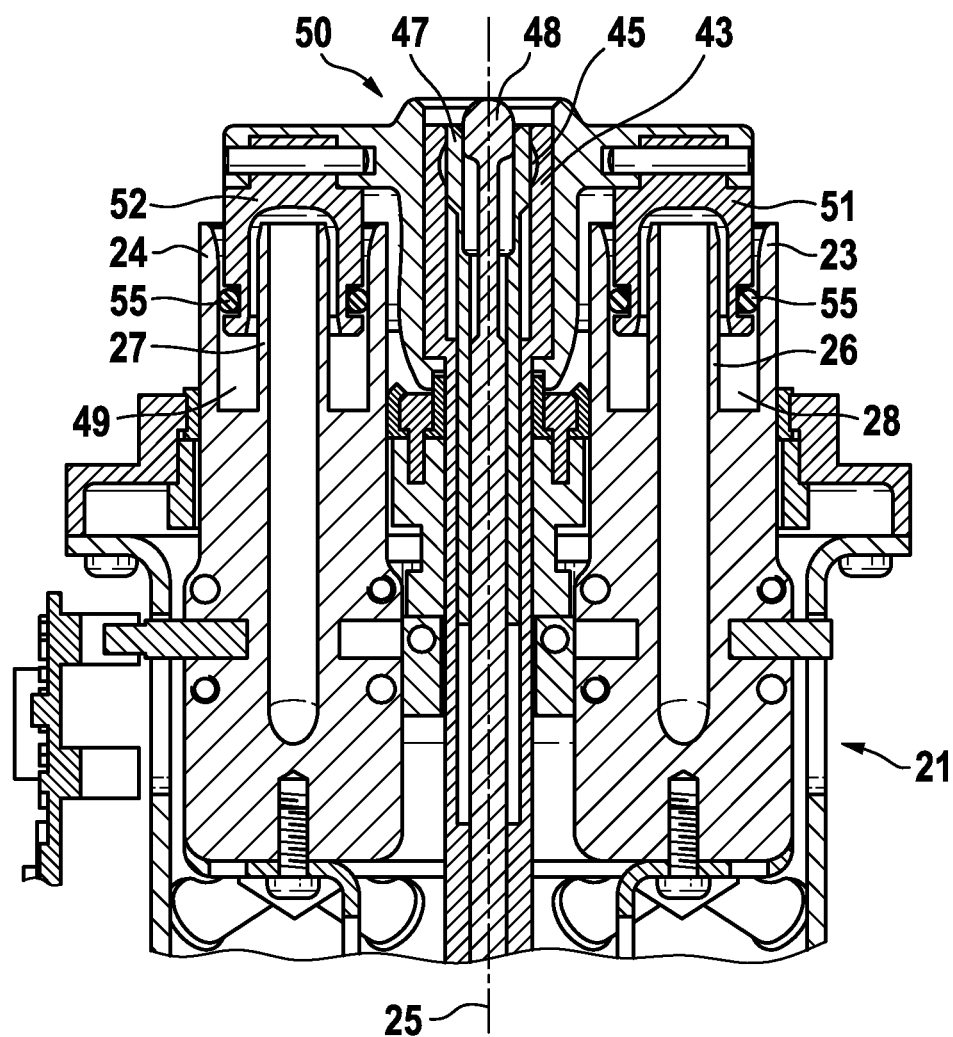
FIG. 7 shows the socket unit of FIG. 2 in a cross-sectional representation, wherein the socket unit is prepared for a rinsing procedure.

Enclosed in each case by the two connection parts 23, 24 is a closed space which is fluid-tight. The fluid-tight closed space forms a rinsing chamber 28, 49 through which a rinsing fluid can be conveyed, which can flow in and flow away via channels not represented in detail (FIG. 7). Rinsing fluid flows through rinsing chambers 28, 49 in order to rinse socket unit B. This is described in detail below.

Connection parts 23, 24 of socket unit B are guided, together with connection pieces 26, 27, in a longitudinally displaceable manner in housing body 21, so that the connection parts and pieces can be advanced out of the housing body or refracted into the housing body. The drive unit for advancing or retracting the connection parts and pieces is not represented in the figures. It can be an electric motor-driven or hydraulic drive unit.

Plug unit A (FIGS. 4 to 6) of device 1 for supplying fresh and for accommodating used dialysing fluid comprises corresponding connectors 29, 30 which are connected fluid-tight to connection pieces 26, 27. Plug unit A comprises a plug body 31 which connects the two connectors 29, 30. Plug body 31 comprises a supply channel 32 which is connected to the one connector 29 and a discharge channel 33 which is connected to the other connector 30. Supply line 16 is connected to connection 17a of supply channel 32 and discharge line 18 of device 1 for supplying fresh and accommodating used dialysing fluid is connected to connection 17b of discharge channel 33. Located between the two connectors 29, 30 is an extension piece 34, with which an initially only loose connection can be produced between plug unit A and socket unit B.

Extension piece 34 comprises a plurality of latching elements 35 which are arranged distributed around the periphery and which are formed integrally at one end of the extension piece. Latching noses 36 are formed at the outer sides of the free ends of latching elements 35. Connectors 29 and 30 comprise contact protection sleeves 37 and 38, which are placed in a latching manner on the two connectors 29, 30 of plug body 31. Connectors 29, 30 are each closed by a membrane 39, 40 which is penetrated by connection pieces 26, 27 of socket unit B.

Housing body 21 of socket unit B comprises a central recess 42 in which a tubular accommodation piece 43 is disposed, into which extension piece 34 of plug unit A can be inserted. Accommodation piece 43 is mounted rotatably around axis 25 with a bearing 44, which is inserted into central recess 42 of housing body 21. Accommodation piece 43 is rotated by a drive unit (not represented).

Tubular accommodation piece 43 comprises a front section 43A extending out of housing body 21 and a rear section 43B extending into the housing body, wherein front section 43A has a larger outer and inner diameter than rear section 43B. Provided on the inner side of the front end of front section 43A of accommodation piece 43, arranged distributed around the periphery, are recesses 45 into which latching noses 36 of latching elements 35 of extension piece 34 are latched when plug unit A is placed loosely onto socket unit B.

A sensing member 47 constituted as a tubular body is guided in a longitudinally displaceable manner in tubular accommodation piece 43, said sensing member being preloaded with a spring (not represented), so that sensing member 47 is pushed back against the spring tension when extension piece 34 is inserted into accommodation piece 43.

A pin-shaped body 48 is guided in tubular sensing member 47 in order to lock extension piece 34 in accommodation piece 43. Pin-shaped body 48 can be advanced and retracted again in the longitudinal direction by a drive unit (not represented), in order to release or lock extension piece 34 in accommodation piece 43.

Figure 4:
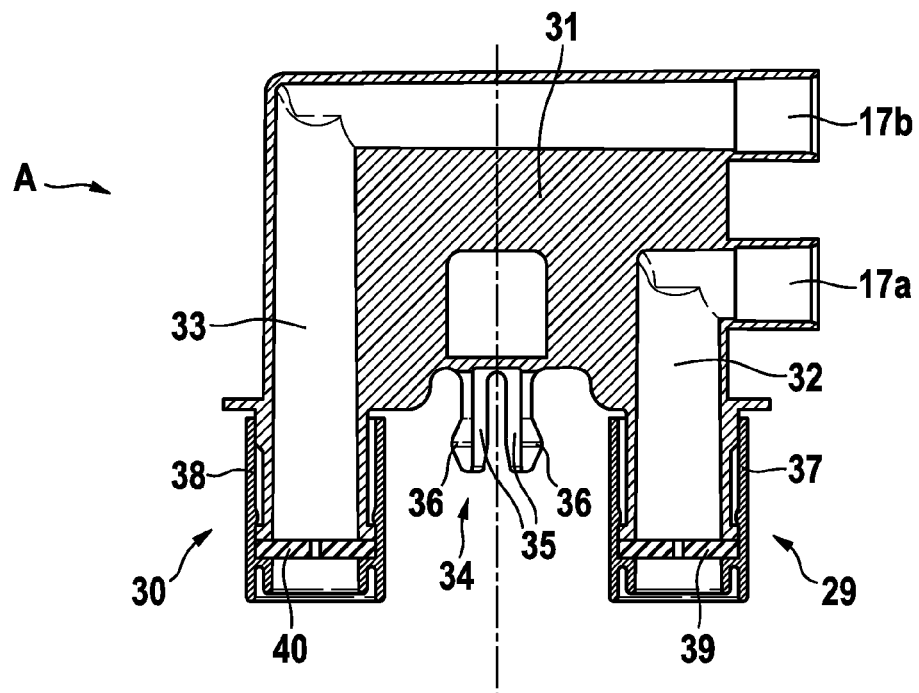
FIG. 4 shows the plug unit and the socket unit of FIG. 2 in a cross-sectional representation, wherein the socket unit is prepared for the connection of the plug unit.
Figure 4:
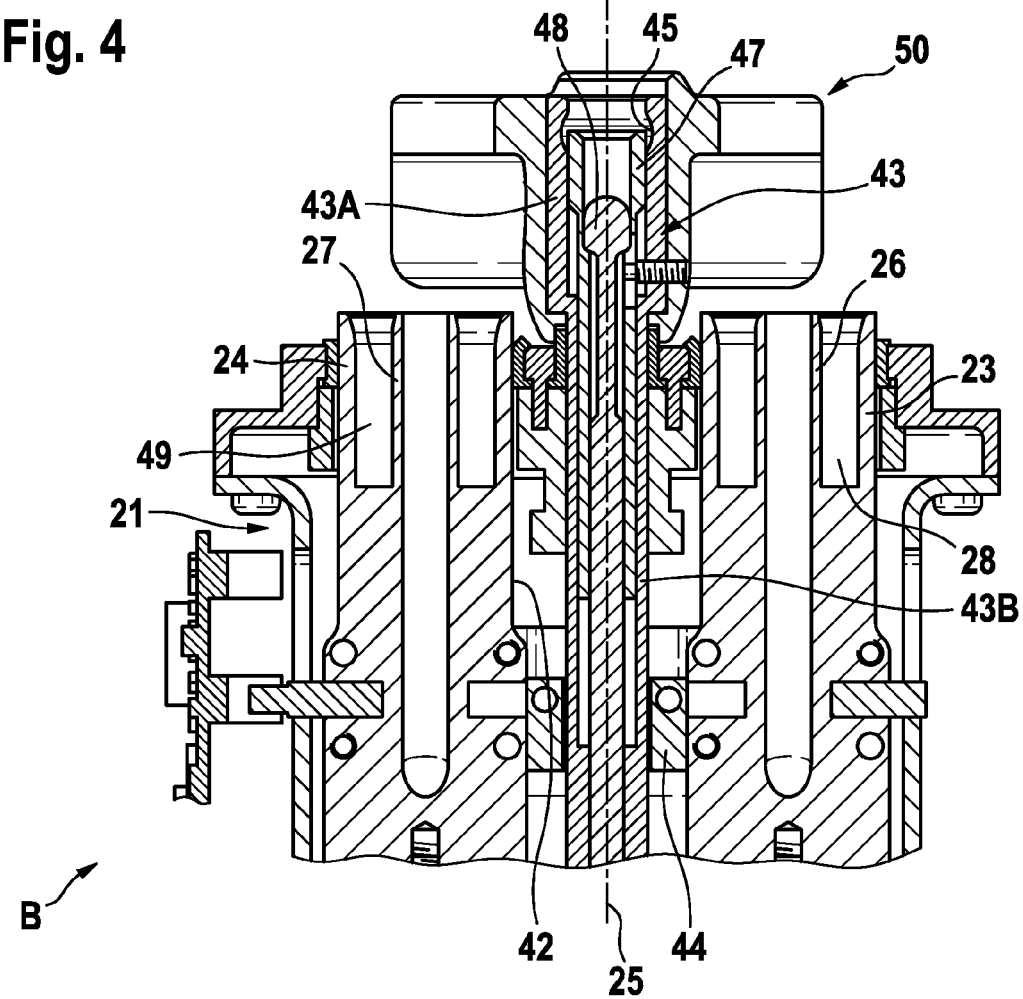

FIG. 4 shows socket unit B in the position in which plug unit A can be placed loosely onto socket unit B. Pin-shaped body 48 is retracted in accommodation piece 43, so that latching elements 35 with latching noses 36 of extension piece 34 can latch into accommodation piece 43 with recesses 45.

Figure 5:
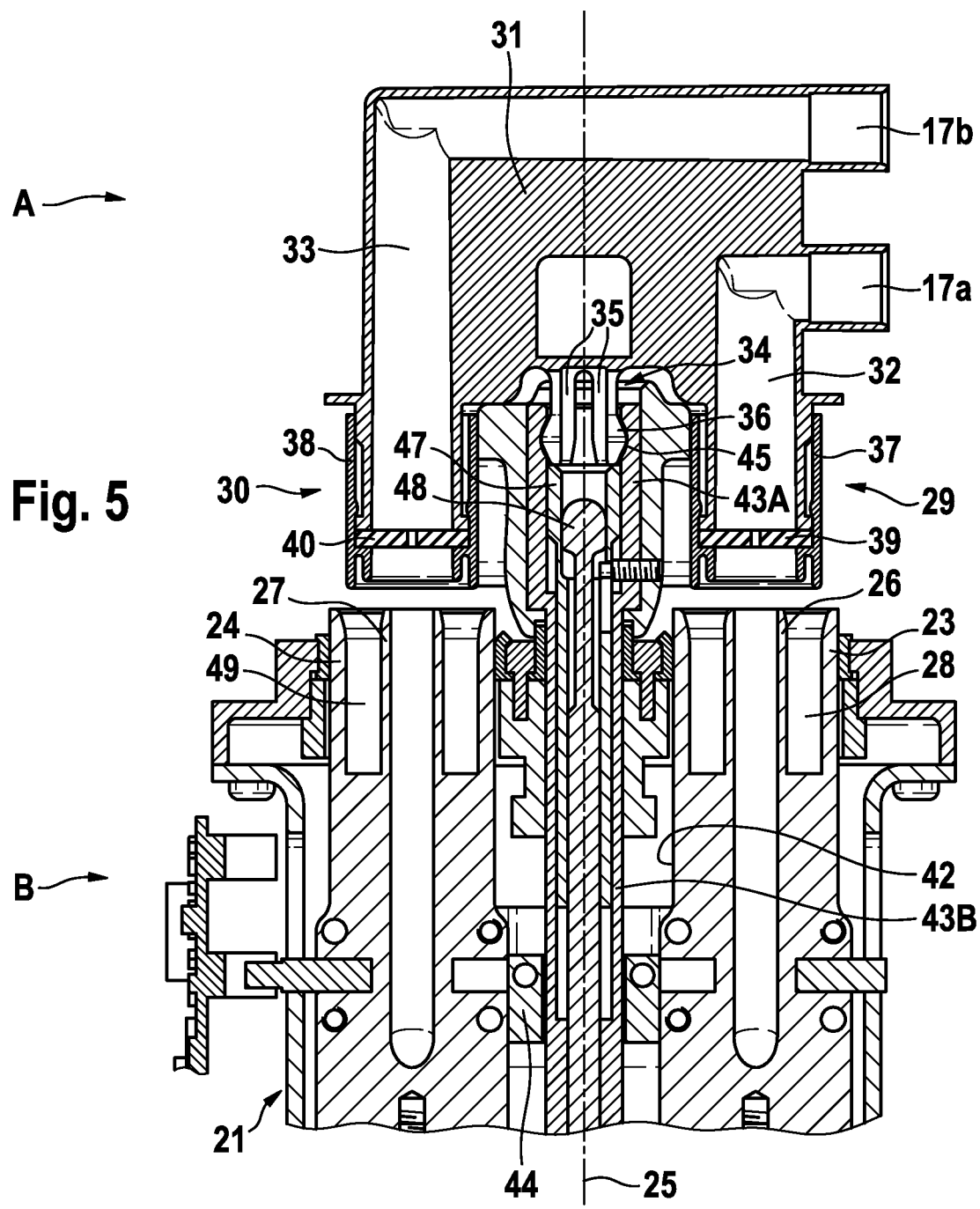
FIG. 5 shows a cross-section through the plug unit and socket unit of FIG. 2, wherein the plug unit is loosely inserted into the socket unit.
Figure 6:
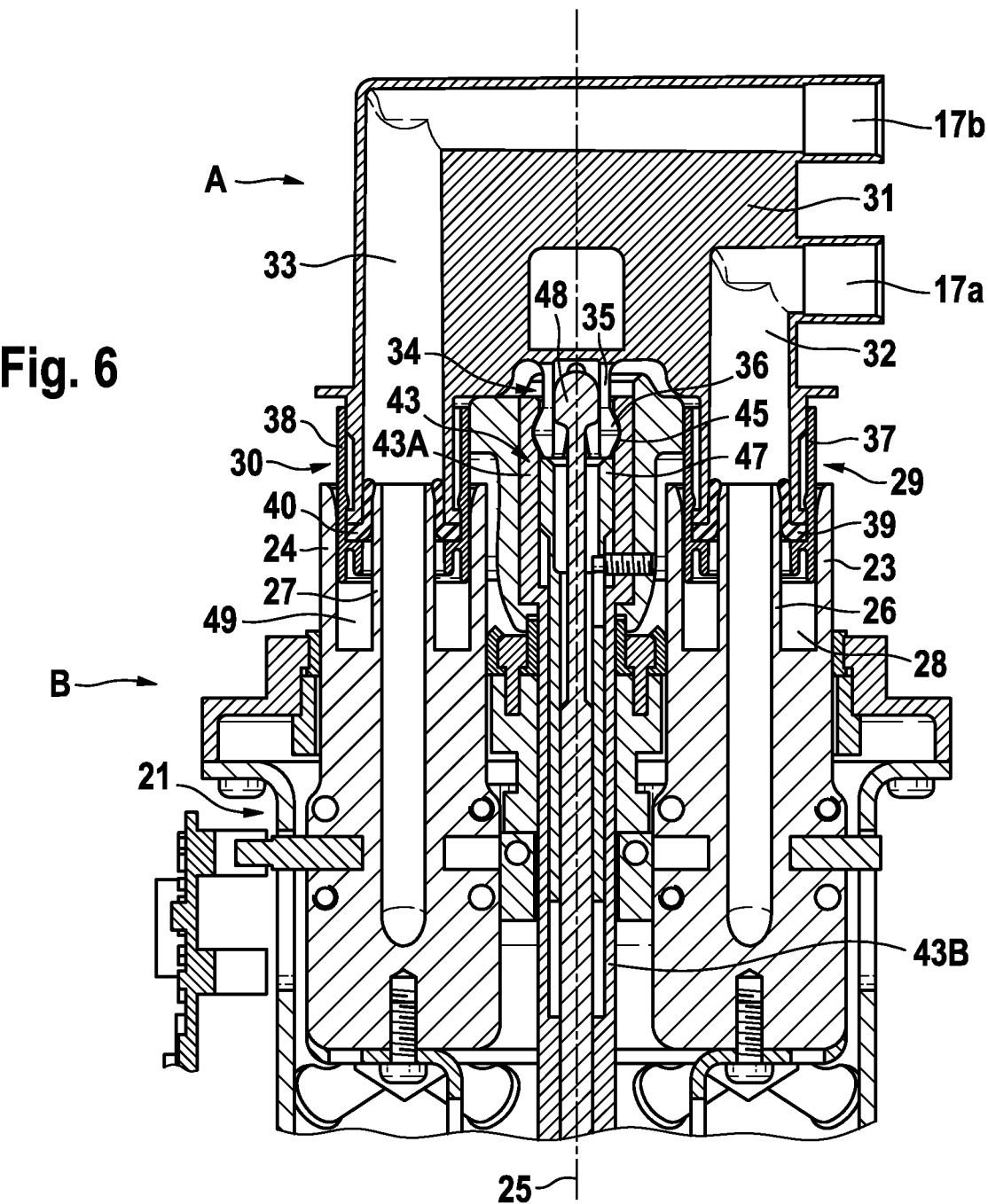
FIG. 6 shows a cross-section through the plug unit and socket unit of FIG. 2, wherein the plug unit is connected to the socket unit, so that the flow connections are produced.

FIG. 5 shows the position in which plug unit A is placed loosely onto socket unit B, wherein extension piece 34 is latched into accommodation piece 43. Plug unit A is thereby held only loosely, without the full connection being produced.

The position of sensing member 47 is monitored by a device (not represented). Since sensing member 47 is pushed back by extension piece 34, it is detected that plug unit A is loosely placed on. When the plug unit is loosely placed on, the drive unit (not represented) is put into operation, as a result of which pin-shaped body 48 is pushed forwards in accommodation piece 43. The initially only loose connection between extension piece 34 and accommodation piece 43 is thus locked. At the same time, connection parts 23, 24 are pushed forwards with connection pieces 26, 27 out of housing body 21. It is also possible for pin-shaped body 48 and connection pieces 26, 27 to be connected to one another and to be moved jointly by a drive unit.

With the displacement of connection parts 23, 24, connection pieces 26, 27 perforate membranes 39, 40 of plug unit A, as a result of which the fluid-tight connections are produced between the connection pieces and connectors. Since plug unit A sits fixedly on socket unit B after the locking of the extension piece with the accommodation piece, the forces occurring when the plug unit and socket unit are connected can be taken up.

The detachment of plug unit A from socket unit B takes place in the reverse sequence. For this purpose, pin-shaped body 48 in accommodation piece 43 and connection parts 23, 24 with connection pieces 26, 27 are retracted in housing body 21, as a result of which the connection between extension piece 34 and accommodation piece 43 is unlocked and connection pieces 26, 27 are pulled out of connectors 29, 30. The unlocking can take place at the same time as the retraction of the connection pieces or before the retraction of the connection pieces.

Socket unit B comprises a closure body 50 for closing the two connection parts 23, 24 in order that a rinsing procedure can be carried out with a rinsing solution.

Closure body 50 comprises two closure parts 51, 52, which are disposed at the same distance from one another as connectors 29, 30 of plug unit A and have the same formation as the connectors of the plug unit. The two closure pieces 51, 52 are closed at their rear end in closure body 50. Closure body 50 comprises semicircular recesses 53, 54 at the two opposite sides at which connectors 29, 30 are not disposed. Recesses 53, 54 each form a right angle with the closure pieces.

Closure body 50 with closure pieces 51, 52 is connected to front section 43A of accommodation piece 43 of socket unit B. Since accommodation piece 43 is mounted rotatably about longitudinal axis 25, closure body 50 with closure pieces 51, 52 can also be rotated about axis 25 by rotating accommodation piece 43 by means of the drive unit (not represented).

FIG. 2 shows closure body 50 with closure pieces 51, 52 in the position in which plug unit A can be placed onto socket unit B. In this position, semicircular recesses 53, 54 are located in front of connection parts 23, 24 and connection pieces 26, 27 of socket unit B, whilst closure pieces 51, 52 are disposed in a plane which lies normal on the plane in which connection parts 23, 24 are disposed. In this position, plug unit A can be inserted into socket unit B.

To start the rinsing procedure, closure body 50 is swivelled with the connectors by rotating accommodation piece 43 through 90° by the drive unit (not represented), so that closure pieces 51, 52 are located in front of connection parts 23, 24. The connection parts are however not yet thereby closed. Connection parts 23, 24 are then advanced out of housing body 21, so that closure pieces 51, 52 are pushed into connection parts 23, 24. Rinsing chambers 28, 49 are thus closed fluid-tight (FIG. 3, FIG. 7) Annular seals 55 can be provided in order to seal closure pieces 51, 52 with respect to connection parts 23, 24. After completion of the rinsing procedure, the connection parts are again retracted. The closure body with the closure pieces can now be rotated back again into the initial position (FIG. 2).

It is advantageous that, after alignment of the closure pieces relative to the connection parts by the relative movement of the closure pieces and connection parts, both parts engage into one another, so that a fluid-tight closure of the rinsing chambers is guaranteed.

Closure body 50 represents a component part of socket unit B. A separate plug or suchlike is not therefore required. Socket unit B permits a fully automatic control both of the connection of plug unit A to socket unit B and also of the starting of the rinsing procedure, so that the handling as a whole is simplified. Since the insertion of plug unit A into socket unit B is detected, the filling or emptying procedure can be started automatically and the plug unit can be released automatically. The rinsing procedure can also be started and ended automatically.

What is claimed is:

1. A medical apparatus, comprising:
a socket unit for connecting a plug unit of a device for supplying medical fluids;
wherein the socket unit comprises at least one connection piece for connection of at least one connector of the plug unit, so that a flow connection for supply or discharge of a fluid can be produced when the at least one connector is connected to the at least one connection piece, and the at least one connection piece is surrounded concentrically by a connection part, thereby forming at least one rinsing chamber, and the socket unit comprises a closure body with at least one closure piece for closing the at least one rinsing chamber;

wherein the closure body is mounted rotatably about a rotational axis, wherein the at least one closure piece on the closure body is disposed at a distance from the rotational axis;

wherein in a first rotational position the at least one closure piece and the connection part lie on a common axis, so that a connection between the at least one closure piece and the connection part for closing the at least one rinsing chamber can be produced by a relative movement of the plug unit and socket unit; and wherein in a second rotational position the at least one closure piece and the connection part are offset with respect to one another, so that the connection between the at least one connector of the plug unit and the at least one connection piece of the socket unit can be produced when the plug unit is inserted into the socket unit.

2. The medical apparatus according to claim 1, wherein the socket unit comprises an accommodation piece and a drive unit for advancing the connection part out of the socket unit and for retracting the connection part into the socket unit.

3. The medical apparatus according to claim 1, wherein the socket unit comprises a first connection part for connection of a first connector of the plug unit and a second connection part for connection of a second connector of the plug unit, so that a first flow connection can be produced for the supply of fluid and a second flow connection can be produced for the discharge of fluid, and the socket unit comprises a closure body with a first closure piece for closing a first rinsing chamber and a second closure piece for closing a second rinsing chamber of the socket unit, wherein the first and second closure pieces are disposed on both sides of the rotational axis.

4. The medical apparatus according to claim 1, wherein the closure body comprises recesses disposed on both sides of the rotational axis for accommodating the connectors of the plug unit when the plug unit is inserted into the socket unit.

5. The medical apparatus according to claim 4, wherein an angle enclosed between the recesses and the connection parts is a right angle.

6. The medical apparatus according to claim 1, wherein the socket unit comprises an accommodation piece, a sensing member and a pin-shaped body for detachable connection of the plug unit and the socket unit.

7. The medical apparatus according to claim 6, wherein an extension piece of the plug unit can be inserted into the accommodation piece.

8. The medical apparatus according to claim 7, wherein the accommodation piece of the socket unit comprises recesses for accommodating latching noses of the extension piece of the plug unit.

9. The medical apparatus according to claim 7, wherein the pin-shaped body, which can be introduced into a recess of the extension piece of the plug unit, is guided in a longitudinally displaceable manner in the accommodation piece, so that the extension piece of the plug unit can be splayed out to produce the connection between the plug unit and the socket unit.

10. The medical apparatus according to claim 6, wherein the sensing member is configured for detecting an extension piece of the plug unit in the accommodation piece of the socket unit.

11. The medical apparatus according to claim 10, wherein the sensing member is spring-loaded such that the sensing member can be displaced against spring tension when the extension piece of the plug unit is introduced into the accommodation piece of the socket unit.

12. The medical apparatus according to claim 7, wherein the accommodation piece is mounted rotatably on the socket unit, and the closure body is fixed to the accommodation piece of the socket unit.

13. The medical apparatus according to claim 1, wherein the medical apparatus is one of a blood treatment apparatus, an extracorporeal dialysis apparatus or an apparatus for peritoneal dialysis.

14. The medical apparatus according to claim 1, wherein the medical apparatus is an apparatus for filling the device for supplying medical fluids for a blood treatment apparatus.

15. An arrangement, comprising:
a device for supplying medical fluids for a medical apparatus; and
the medical apparatus according to claim 1;
wherein the device for supplying medical fluids comprises a plug unit for connection to the socket unit of the medical apparatus.

* * * * *